United States Patent [19]

Highley et al.

[11] 4,338,295

[45] Jul. 6, 1982

[54] HAIR SETTING AND BODYING COMPOSITION AND METHOD

[75] Inventors: Derek R. Highley, North Weymouth; Jayant N. Sane, Framingham, both of Mass.

[73] Assignee: The Gillette Company, Boston, Mass.

[21] Appl. No.: 206,126

[22] Filed: Nov. 12, 1980

[51] Int. Cl.³ .......................... A61K 7/09; A61K 7/11
[52] U.S. Cl. ............................................ 424/71; 132/7
[58] Field of Search ...................................... 424/70, 71

[56] References Cited

U.S. PATENT DOCUMENTS 2,899,965 8/1959 McGoldrick et al. ................. 424/71
3,242,118 3/1966 St. Clair et al. .................... 260/29.3
3,661,161 5/1972 Kalopissis et al. ...................... 132/7
4,243,659 1/1981 Balingit ................................. 424/70
4,278,659 7/1981 Breuer .................................. 424/71

OTHER PUBLICATIONS

"The Merck Index," 9th Edition, No. 7951 (1976).

Primary Examiner—Dale R. Ore
Attorney, Agent, or Firm—Mandel E. Slater

[57] ABSTRACT

Compositions and method for imparting shampoo resistant body and settability to human hair comprising the application of an aqueous solution containing a precondensate of glyceraldehyde and resorcinol under conditions promoting in situ polymerization. Tendency for yellowing of gray hair is substantially avoided by incorporation in the solution of urea.

10 Claims, No Drawings

HAIR SETTING AND BODYING COMPOSITION AND METHOD

BACKGROUND OF THE INVENTION

This invention relates to hair setting and bodying compositions and methods, and relates more particularly to the in situ polymerization of certain precondensates which are caused to penetrate into the fiber structure of hair.

In copending application Ser. No. 083,137, now U.S. Pat. No. 4,278,659 the disclosure of which is herein incorporated by reference, it is shown that hair tresses treated with aqueous mixtures containing a precondensate of glyceraldehyde and resorcinol exhibit excellent and lasting set holding to hair with significant increases in body. These improved properties are resistant to high humidity conditions and removal by normal shampooing. The treated hair is similar to intact hair in fell, luster, mechanical strength, and wet and dry combing characteristics. The stability of most hair colors to light exposure appears to be at least equal to that of intact hair.

We have found, however, that in applying the above treatment to hair that is substantially gray, for example about 50% gray, the hair in time tends to undergo a certain yellowing, which is undesirable.

SUMMARY OF THE INVENTION

Accordingly it is the primary object of this invention to provide a treatment which will impart to human hair the property of multistylability, while at the same time avoiding the yellowing of gray hair. Multistylability is essentially a combination of two properties: a capability for maintaining an imparted set for a considerable length of time, even under conditions of high humidity, and the capability of being restyled into new configurations after wetting of the hair. Once restyled, multistylable hair will maintain its new configuration even after exposure to high humidities. In this manner it differs from both intact and permanently waved hair inasmuch as either will revert at high humidities to an original style, i.e., intact hair to its natural configuration and waved hair to the one which has been imparted during the permanent waving process.

With the above object in view, according to the invention, hair which may have been previously washed is treated with an aqueous solution containing a precondensate of glyceraldehyde and resorcinol, plus urea. After the treating solution has had a chance to penetrate and further condense within the hair fibers, the hair tresses take on the attributes of multistylability as described above. Such treated tresses can be shampooed and reset on rollers through several cycles without losing the imparted multistylability, exhibiting improved set retention when compared in intact, water-set tresses, and without noticeable yellowing of gray hair.

Tresses of straight hair treated in accordance with the invention, when wetted and set straight, as for example by combing out and drying while hanging free with a weight attached, remain straight, even under conditions of high humidity in contrast to intact curly hair or permanently waved tresses which revert to curly configurations upon wetting.

DESCRIPTION OF THE PREFERRED EMBODIMENTS

Prior to the application to the hair, the glyceraldehyde and resorcinol are heated together in the presence of boric or silicic acid to bring about the partial conversion of the monomeric species to a low molecular weight, oligomeric precondensate species. The conditions under which the precondensate is formed and proportions of the reactant species are very important in achieving an optimum result, although the urea can be added prior to or subsequent to formation of the precondensate.

To form the precondensate referred to above, it is preferred to heat an aqueous solution containing glyceraldehyde, resorcinol and boric or silicic acid. In investigating the effects of varying the ratio of glyceraldehyde to resorcinol in the practice of the invention, we have found that the optimum molar ratio is about 1:1, with the preferred range being 4:1 to 1:4. It is possible, however, to achieve useful set holding improvements employing ratios ranging from 19:1 to 1:19. While, in general, the effectiveness of the treatment increases with increasing concentration of glyceraldehyde and resorcinol, about 10% is preferred. Little additional improvement is realized by employing higher concentrations, although as much as 20% by weight combined glyceraldehyde and resorcinol in the solution may be used to form the precondensate. It is possible to use as little as 0.5% by weight combined glyceraldehyde and resorcinol and still achieve a useful result.

The urea may be present in amounts from about 0.1% to 20% by weight of the total composition. While not intending to be bound by any particular theory of the benefit conferred by the urea, it is proposed that the hair yellowing is associated with the presence of free or unreacted aldehyde in the composition, since the reaction between the glyceraldehyde and the resorcinol is not complete. The urea may be reacting with and tying up the free aldehyde, so that the aldehyde is unavailable to cause yellowing; this it must do without degrading the hair treating properties of the composition. Thus a high ratio of glyceraldehyde to resorcinol will result in much free aldehyde and call for the higher concentrations of urea, and conversely. Even with a low ratio, there will still be free aldehyde, calling for at least a modest amount of urea in any event. When the ratio is 1:1, about 0.5% to 2% urea gives particularly good results.

The proportional relationship between boric or silicic acid and glyceraldehyde has also been found to be important in achieving an optimum result. Whereas a 1:1 molar ratio of glyceraldehyde to acid has been found to be best, a range of ratios from 4:1 to 1:1.5 can be used in the practice of the invention.

It has also been found that the result can be further improved if the pH of the reactant mixture prior to reflux is reduced by the addition of an acid stronger than the boric or silicic acid component. While studies have shown the pH reduction by the addition of any stronger acid, organic or inorganic, is advantageous, hydroxycarboxylic acids such as tartaric, mandelic, salicylic, and especially citric acid are preferred. The amount of strong acid used should be sufficient to reduce the pH to about 1.6–1.8 to maximize the enhanced result.

In forming the glyceraldehyde-resorcinol precondensate referred to herein, it is preferred to reflux the aqueous mixture of glyceraldehyde, resorcinol, acid (boric or silicic) and pH-adjusting acid for about 90 minutes. Heating for a longer period of time appears to reduce efficacy, probably by the formation of an increased proportion of higher molecular weight species which are not able to penetrate hair fibers as readily as the lower molecular weight precondensate species formed during a shorter reflux. It is, however, possible to reflux for 24 hours or longer and still see a practically useful result. Such long reflux time, however, may result in the formation of undesirable precipitates in the reaction mixture which should preferably be removed before application to the hair.

The urea can be added before the mixture is refluxed or afterwards. In the latter case it is preferable to reflux for an additional period, although in such case reduction in yellowing is noted even without additional reflux. 90 minutes total reflux when the urea was added initially, and 90 minutes initial reflux followed by urea addition and 30 minutes extra reflux, both gave particularly good results in reducing yellowing while maintaining the hair treatment advantages of the composition.

In product applications where it is desirable to have the user of the composition prepare it freshly before application to the hair, a useful amount of precondensate can be formed by simply dissolving the active ingredients in boiling water and waiting a few minutes for the resulting solution to cool to body temperature before application.

For the purposes of ease of application and to enable the user to apply enough of the treating composition to the hair to insure the optimum result, any cosmetically acceptable thickener may be added which is non-reactive with the other ingredients and stable at the pH levels at which the invention is practiced. Approximately 1% by weight guar gum can be used, which is added after refluxing the other ingredients.

In applying the compositions of this invention to the hair, it is desirable to first shampoo the hair with any good quality commercially available product. After shampooing and rinsing, the hair may be towel dried if desired. The treating composition, which should be applied to the hair in a quantity sufficient to saturate it, may be applied in any convenient fashion, such as direct application from a plastic squeeze bottle or by dabbing with a saturated sponge or cotton applicator.

Following application of the treating composition to the hair, it is necessary to permit it to diffuse through the fibers for 15 to 60 minutes. During this period, it is desirable to wrap the hair in a towel or plastic or other turban to reduce evaporative cooling and as an aid in retaining heat produced by the scalp. Externally applied heat, as from a hair dryer, may also be employed during the diffusion step.

After the diffusion step the hair should be thoroughly rinsed, this time to remove any undiffused treating composition from the individual fibers. Following towel drying of the treated hair, it is then preferably heated to complete conversion of the glyceraldehyde-resorcinol precondensate to the final higher molecular weight condensate product which imparts the desired mechanical properties to the modified hair fibers. This can be accomplished conveniently by wrapping the towel dried hair on conventional hair setting curlers, followed by drying with either a helmet-type or hand-held hair dryer. The diameter of the rollers employed will determine in part the final styled result with smaller diameter rollers providing a tighter final curl result. Rollers of $\frac{3}{4}$ to 2 inches in diameter are suitable for the average range of hair styles.

It is also possible to bring about conversion of the precondensate by air drying or blow drying the hair in its normally straight configuration, i.e. without first wrapping it on setting rollers. In this case the dried hair can at any subsequent time be set on rollers after first wetting it with water, or it may alternatively be set dry on heated rollers.

While the use of heat has been mentioned in drying the treated hair during the condensation step, it is possible to achieve a useful result by simply allowing the treated hair, after the post-diffusion rinsing step, to dry at room temperature either in roller set or straight form. In the absence of heating completion of the condensation step takes a longer period of time, but the end result is essentially the same.

EXAMPLE I

A glyceraldehyde-resorcinol precondensate was prepared by refluxing an aqueous solution of 5% by weight glyceraldehyde, 5% resorcinol, 3.4% boric acid (making it equimolar in glyceraldehyde and boric acid), 1% citric acid, and 1% urea for 90 minutes. The pH of the resultant mixture was 1.78. The resulting composition was evaluated for curl retention on hair tresses and on human subjects according to the methodologies described in copending application Ser. No. 083,137, with the result that the composition was substantially at parity with the composition without the urea. Observer panels noted no significant difference in yellowing of gray hair between the test composition with urea and untreated controls, but did note a significant preference (less yellow) for the test composition with urea as compared to a like composition without urea.

EXAMPLES II, III, IV

A glyceraldehyde-resorcinol precondensate was prepared as described in Example I, except that the 1% urea was added after the initial 90 minutes reflux, followed by additional refluxing for times of 0, 15, and 30 minutes, respectively. In all the examples curl retention was substantially at parity with control samples treated with compositions refluxed for 90 minutes and having no urea added. Gray hair treated with the compositions of these examples was less preferred (more yellow) then untreated controls, but preferred (less yellow) over compositions without the urea; results improved with increasing reflux times after addition of the urea. In clinical tests with the composition of Example IV neither test subjects nor their beauticians detected any yellowing or discoloration for at least four weeks after treatment.

What is claimed is:

1. In a hair treating composition for imparting improved setting properties comprising an aqueous solution containing about 0.5 to 20% by weight of a mixture of glyceraldehyde, resorcinol, and an oligomeric precondensate of glyceraldehyde and resorcinol, said composition being prepared by heating an aqueous mixture containing glyceraldehyde, resorcinol, and an acid selected from the class consisting of boric acid and silicic acid, the molar ratio of glyceraldehyde to resorcinol being about 19:1 to 1:19 and the molar ratio of glyceraldehyde to said acid being about 4:1 to 1:1.5; wherein the improvement comprises including in said composition about 0.1% to 20% by weight of urea.

2. A hair treating composition as defined in claim 1, containing, in addition, a hydroxycarboxylic acid selected from the group consisting of tartaric, mandelic, salicylic and citric acids, the quantity of said hydroxycarboxylic acid being sufficient to reduce the pH of said composition to a level lower than the pH level imparted by said boric or silicic acid.

3. A hair treating composition as defined in claim 1, in which the molar ratio of glyceraldehyde to resorcinol is about 1:1, the molar ratio of glyceraldehyde to said acid is about 1:1, the concentration of urea is about 0.5% to 2% by weight, and containing, in addition, a hydroxycarboxylic acid selected from the group consisting of tartaric, mandelic, salicylic and citric acids, the quantity of said hydroxycarboxylic acid being sufficient to reduce the pH of said composition to about 1.6–1.8.

4. In a method of treating hair to impart improved setting properties, comprising the application of a composition comprising an aqueous solution containing about 0.5 to 20% by weight of a mixture of glyceraldehyde, resorcinol, and an oligomeric precondensate of glyceraldehyde and resorcinol, said composition being prepared by heating an aqueous mixture containing glyceraldehyde, resorcinol, and an acid selected from the class consisting of boric acid and silicic acid, the molar ratio of glyceraldehyde to resorcinol being about 19:1 to 1:19 and the molar ratio of glyceraldehyde to said acid being about 4:1 to 1:1.5, wherein the improvement comprises including in said composition about 0.1% to 20% by weight of urea.

5. A method as defined in claim 4, in which said composition contains, in addition, a hydroxycarboxylic acid selected from the group consisting of tartaric, mandelic, salicylic, and citric acids, the quantity of said hydroxycarboxylic acid being sufficient to reduce the pH of said composition to a level lower then the pH level imparted by said boric or silicic acid.

6. A method as defined in claim 4, in which the molar ratio of glyceraldehyde to resorcinol is about 1:1, the molar ratio of glyceraldehyde to said acid is about 1:1, the concentration of urea is about 0.5% to 2%, and in which the composition contains, in addition, a hydroxycarboxylic acid selected from the group consisting of tartaric, mandelic, salicylic, and citric acids, the quantity of said hydroxycarboxylic acid being sufficient to reduce the pH of said composition to about 1.6–1.8.

7. In a method for the preparation of a hair treating composition for imparting improved setting properties, comprising heating an aqueous solution containing about 0.5 to 20% by weight of a mixture of glyceraldehyde and resorcinol and containing, in addition, an acid selected from the class consisting of boric acid and silicic acid to form an oligomeric precondensate of glyceraldehyde and resorcinol, the molar ratio of glyceraldehyde to resorcinol being about 19:1 to 1:19 and the molar ratio of glyceraldehyde to said acid being about 4:1 to 1:1.5; wherein the improvement comprises adding to said solution about 0.1% to 20% by weight of urea.

8. A method as defined in claim 7, in which the mixture contains, in addition, a hydroxycarboxylic acid selected from the group consisting of tartaric, mandelic, salicylic, and citric acids, the quantity of said hydroxycarboxylic acid being sufficient to reduce the pH of said composition to a level lower than the pH level imparted by said boric or silicic acid.

9. A method as defined in claim 7, in which the molar ratio of glyceraldehyde to resorcinol is about 1:1, the molar ratio of glyceraldehyde to said acid is about 1:1, the concentration of urea is about 0.5% to 2%, and in which the mixture contains, in addition, a hydroxycarboxylic acid selected from the group consisting of tartaric, mandelic, salicylic, and citric acids, the quantity of said hydroxycarboxylic acid being sufficient to reduce the pH of said mixture to about 1.6–1.8.

10. A method as defined in any of claims 7, 8, 9, in which the urea is added after first heating said solution, with or without additional heating.

* * * * *